United States Patent [19]

Rushbrook et al.

[11] 4,357,174
[45] Nov. 2, 1982

[54] SLAB GEL DESTAINING METHOD

[75] Inventors: Julie I. Rushbrook; Reichard D. Feinman, both of Brooklyn, N.Y.

[73] Assignee: Research Foundation of the State Univ. of NY, Albany, N.Y.

[21] Appl. No.: 253,393

[22] Filed: Apr. 13, 1981

Related U.S. Application Data

[63] Continuation of Ser. No. 99,834, Dec. 3, 1979, abandoned.

[51] Int. Cl.³ .............................................. B01D 15/00
[52] U.S. Cl. ...................................... 134/10; 210/694
[58] Field of Search ........................... 134/111, 10, 34; 210/282, 287, 484, 694, 497.01

[56] References Cited

U.S. PATENT DOCUMENTS

| 264,463 | 9/1882 | Koeppel | 210/282 |
| 2,110,318 | 3/1938 | Baruch | 210/287 |
| 3,392,837 | 7/1968 | Sanzenbacher | 210/282 |
| 3,534,747 | 10/1970 | Hoefer | 134/111 |
| 3,930,880 | 1/1976 | Hoefer | 134/111 |
| 4,005,010 | 1/1977 | Lunt | 210/282 |

Primary Examiner—Ivars C. Cintins
Attorney, Agent, or Firm—Omri M. Behr

[57] ABSTRACT

A destainer for electrophoresis slab gels includes a housing having a height along its vertical axis equal to or less than its length and width thereby forming relatively short end walls which are provided with a plurality of apertures. A stain absorbing material is placed within the housing and prevented from leaving the housing by means of a porous material which permits the free flow of liquid into and out of the housing.

8 Claims, 4 Drawing Figures

SLAB GEL DESTAINING METHOD

This application is a continuation of application Ser. No. 099,834, filed Dec. 3, 1979, now abandoned.

BACKGROUND OF THE INVENTION

1. Field of the Invention

The present invention relates to a destainer for slab gels that readily removes the stain particles without the use of elaborate pumping and filtering equipment.

2. Description of the Relevant Art

A destainer for disc electrophoresis rods utilizing circulating liquid is disclosed in U.S. Pat. No. 3,534,747 issued to P. S. Hoefer on Oct. 20, 1970. The device disclosed therein is used as a destainer for disc electrophoresis rods which are contained in tubes including a cylindrical container for holding acetic acid that has a magnetic stirring rod at its base to set up circulation. The rods are placed on a flange-type holder which mates with the walls of the container to force substantially all upward circulating liquid through the tubes. The holder includes an inner column having openings at its top to allow for downward circulation of the liquids through both an activated charcoal filter and for free movement down toward the stirring rod.

The same basic principle is used in the device as disclosed in U.S. Pat. No. 3,930,880 issued to Hoefer on Jan. 6, 1976 which relates to a destainer for electrophoresis slab gels. The slab gels are placed in flexible mesh and rolled into cylindrical shapes and then inserted into slab holding tubes. The slab holding tubes are placed in the flowpath of a washing liquid which flows past the slab gels and then through a return path containing a filter for removing stain particles washed away from the slab gels. A magnetic stirrer draws fluid through the filter forcing it through the slab holding tubes and into the return flow path thereby forming a continuous flow path for destaining slab gels contained entirely within a cylindrical outside container. This device limits the size of the slab to be treated, is not designed to accommodate swelling of the gel during destaining and can produce nonuniform destaining across the gel during the destaining process, which may be of concern if quantification of bands is desired.

Heretofore when destaining a slab gel in a flat plate by diffusion destaining, the destaining liquid was poured over the slab gel and it was agitated. As the liquid became contaminated after a short period of time it was poured off and replaced with new liquid. However, this process was time consuming in terms of manual labor and time to destain the gel, was wasteful of destaining solution and inconvenient if strict standardization of the staining process is desired i.e. from gel to gel. Thus, the more elaborate devices discussed hereinbefore came into use.

SUMMARY OF THE INVENTION

An object of the present invention is to provide a slab gel diffusion destainer which is small in size and capable of being used in a flat dish.

Another object of the present invention is to provide a relatively inexpensive slab gel destainer which may be thrown away after use or alternatively refilled with a stain absorbing material and reused.

A further object of the present invention is to provide a slab gel diffusion destainer that is capable of being used with slab gels of various sizes which are kept in a flat position during the destaining process.

A still further object of the present invention is to provide a slab gel destainer which speeds up the process of destaining a slab gel in a flat dish.

The slab gel destaining apparatus disclosed herein overcomes the shortcomings found in the prior art by providing an inexpensive slab gel destaining apparatus which may be used with a flat dish and an inexpensive shaker frequently found in the lab.

The slab gel whose initial size is not limited, is maintained in a flat position, is free to swell during destaining, and destains uniformly across its surface, unlike the conditions occurring in the Hoefer apparatus. Furthermore, compared with destaining a slab gel in a flat dish with manual changing of solution, manual labor and time of destaining are reduced, destaining solution is conserved and the destaining process can be standardized with regard to time if desired.

A slab gel destaining apparatus, according to the principles of the present invention, comprises in combination a hollow housing having a height along its vertical axis equal to or less than its length and width thereby, forming relatively short end walls which are provided with a plurality of apertures. A stain absorbing material is disposed within the housing and is retained therein by a porous material disposed along the inner walls of the housing to cover the apertures, thereby preventing the stain absorbing material from leaving through the apertures while permitting the destaining liquid to freely flow into and out of the housing.

BRIEF DESCRIPTION OF THE DRAWINGS

In order that the invention may be more fully understood, it will now be described, by way of example, with reference to the accompanying drawing in which.

DESCRIPTION OF THE PREFERRED EMBODIMENT

Figure 1:
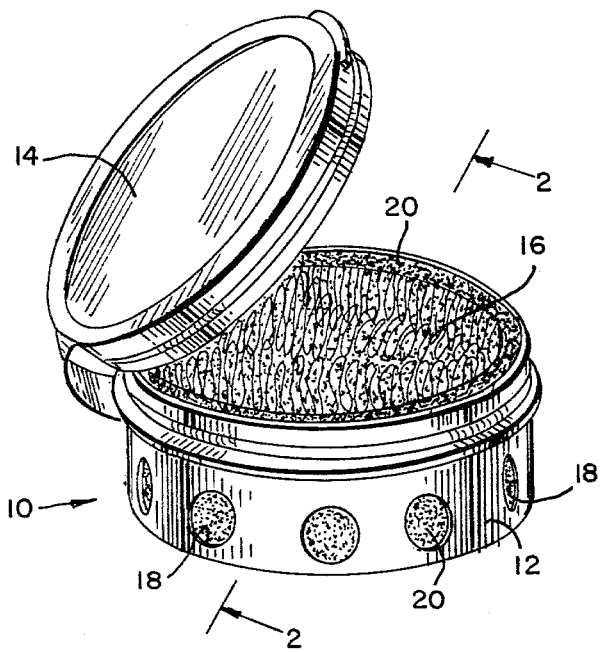
FIG. 1 is a pictorial representation of a slab gel destaining apparatus according to the principles of the present invention, with its cover opened to disclose the destaining materials.
Figure 2:
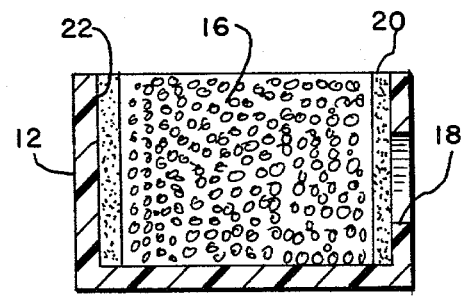
FIG. 2 is a cross-sectional view taken along the line 2—2 of FIG. 1.

Referring now to the figures, and in particular to FIGS. 1 and 2, a slab gel destaining apparatus 10 has a hollow housing 12, which in the preferred embodiment is cylindrically shaped. The housing 12 has a cover 14 attached thereto in a conventional manner. The cover 14 fits tightly on the housing 12 preventing any stain absorbing material 16 from escaping therefrom. Preferably, the housing 12 and cover 14 are formed in one integral piece from polyethylene. A preferred container is 2.2 cm in height and 3.8 cm in diameter and is provided with a plurality of apertures 18 all around the circumference of the housing 12. Alternatively, two large apertures about the circumference to permit the free flow of destaining fluid therethrough may be utilized.

An elongated strip 20 polypropylene mesh having mesh openings between 200 and 500 microns, preferably with a 250 micron mesh opening, is placed along the inner wall 22 of the housing 12, thus preventing the stain absorbing material 16 from falling out of the apertures 18. The openings in the porous elongated strip however permit liquid to freely flow into and out of the housing 12 through the apertures 18.

Figure 3:
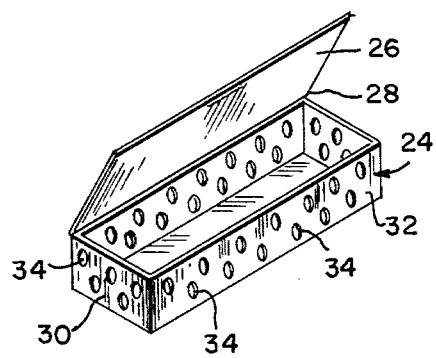
FIG. 3 is a pictorial representation of an alternative housing construction, according to the principles of the present invention.

Referring now to FIG. 3 which discloses an alternative embodiment of the housing 24. The housing 24 is rectangular shaped and includes a cover 26 integrally formed therewith by means of a living hinge 28. The end walls 30 and 32 are provided with a plurality of apertures 34 to permit the free flow of liquid into and out of the housing 24 while retaining the stain absorbing material therein, not shown, by means of a elongated strip, not shown, positioned around the inner wall of the housing 24. The elongated strip and stain absorbing material is exactly the same as that shown in FIG. 1.

Preferably the stain absorbing material is activated charcoal suitably 14 by 40 mesh, although unactivated charcoal may also be used as a destaining material. The preferred configuration improved stability during agitation with the destaining liquid and gel in a flat dish, as well as minimizing the amount of destaining liquid required.

Figure 4:
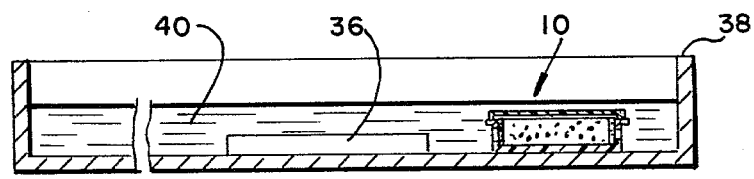
FIG. 4 is a cross-sectional view of the slab gel destaining apparatus utilized with a slab gel in a flat dish.

Referring now to FIG. 4, a slab gel 36 is positioned in a flat dish 38 with the destaining apparatus 10 and covered with a destaining liquid 40 suitably 5% t-butanol, 7.5% acetic acid. The flat dish 38 is placed upon a shaker normally found in the laboratory (not shown) to provide gentle agitation of the liquid 40.

In operation, the slab gel of sodium dodecylsulfate-containing polyacrylamide used in an electrophoresis process is one of the most commonly used procedures for the analysis of proteins at the present time. Following electrophoresis, proteins are visualized by staining usually with the dye Coomassie Brilliant Blue R-250 in the presence of protein precipitating agents, followed by destaining. The SDS slab gel electrophoresis procedure utilizes a gel of approximately 13 by 16 cm placed in a dish which is stained overnight in 0.1% Coomassie BB R-250, 50% methanol, 10% acetic acid and destained in 5% t-butyl alcohol, 7½% acetic acid. The staining solution is then removed from the dish, the gel rinsed with deionized water to remove excess dye, and the destaining solution is added thereto for a period of approximately eight hours with continuous mild agitation.

The destaining apparatus 10 is placed in the dish as shown in FIG. 4 and remains there for the complete period of agitation. The stained gel slab is covered with a sufficient amount of solvent whereby the solvent dissolves the uncombined dye on the gel and circulates through the carbon in the destaining apparatus. Since the affinity of the carbon for the dye is greater than the affinity of the gel for the dye eventually the gel is completely cleaned of dye. The capacity of the charcoal to absorb the die is large and it may be reused over and over again, providing satisfactory results for six months or more, depending upon its frequency of use. Thereafter, the destaining apparatus 10 may be disposed of and replaced with a new unit or, alternatively, the housing may be opened and the charcoal replaced. The destaining of the gel to a background dye level suitably for photography occurs in approximately eight hours and further destaining (over night) will reduce the background staining to zero though this is probably to be avoided. Normally, fresh destaining solution is prepared for each new gel, but this may not be necessary since the components of the destaining solution, acetic acid and t-butyl alcohol are chosen to maintain a stable system i.e. minimize the rate of ester formation.

Hereinbefore has been disclosed a slab gel destaining apparatus for use with slabs destained in a flat dish, which is inexpensive, provides a means for readily absorbing stain and provides the necessary results in a reduced period of time. It will be understood that various changes in the details, materials, arrangement of parts and operating conditions which have been herein described and illustrated in order to explain the nature of the invention may be made by those skilled in the art within the principles and scope of the present invention.

Having thus set forth the nature of the invention, what is claimed is:

1. A process of destaining stained slab gel comprising the steps of:
   (a) providing a destaining apparatus comprising in combination
      (i) a hollow housing having a height along its vertical axis equal to or less than its length and width thereby forming relatively short end walls, said end walls being provided with a plurality of apertures;
      (ii) stain absorbing material means disposed within said housing;
      (iii) means positioned to cover said apertures for preventing said stain absorbing material means from leaving said housing means while permitting destaining liquid to freely flow therethrough and;
      (iv) a fluid containing means comprising a base and having a length and width sufficient to contain therein the slab to be destained when said slab is laid flat upon the base thereof, said fluid containing means having a depth sufficient to permit destaining fluid to cover said slab, and further being of sufficient size to contemporaneously accomodate said slab and said housing when said housing is set therein having its vertical axis perpendicular to the base of said fluid containing means;
   (b) placing the slab gel to be destained upon the base of said fluid containing means,
   (c) providing sufficient destaining fluid to said fluid containing means to cover said slab,
   (d) agitating said fluid containing means whereby the destaining fluid is caused to circulate through the stain absorbing material in the housing until all unreacted stain has been removed from said stained slab gel.

2. A process according to claim 1 wherein said hollow housing means is cylindrically shaped with the circumferential wall thereof being provided with said apertures.

3. A process according to claim 1 wherein said stain absorbing material means is charcoal.

4. A process according to claim 1 wherein said stain absorbing means is activated charcoal granules.

5. A process according to claim 1 wherein said means to cover said apertures is an elongated strip of porous material disposed about the inner walls of said housing means.

6. A process according to claim 5 wherein said porous material is polypropylene mesh.

7. A process according to claim 6 wherein said mesh openings are between 200 and 500 microns.

8. A process according to claim 1 wherein said housing means is polyethylene and includes an integrally formed cover.

* * * * *